United States Patent

Haehn

Patent Number: 5,433,928
Date of Patent: Jul. 18, 1995

[54] ABSORPTION COLUMN WITH INTERNAL MIXING CHAMBER FOR ABSORPTION OF ACETYLENE

[75] Inventor: Peter-Clemens Haehn, Geretsried, Germany

[73] Assignee: Linde Aktiengesellschaft, Wiesbaden, Germany

[21] Appl. No.: 43,094

[22] Filed: Apr. 5, 1993

Related U.S. Application Data

[60] Division of Ser. No. 980,868, Nov. 24, 1992, Pat. No. 5,336,838, which is a continuation of Ser. No. 933,590, Aug. 24, 1992, abandoned.

[30] Foreign Application Priority Data

Aug. 23, 1991 [DE] Germany ............ 41 27 988.3

[51] Int. Cl.⁶ .................................................. B01J 8/04
[52] U.S. Cl. .................................... 422/215; 202/176; 203/DIG. 6; 203/DIG. 9; 261/114.1; 261/18.1; 422/211; 422/213; 422/255; 422/256; 422/257
[58] Field of Search ............................ 422/255–257, 422/224, 211, 213, 215; 261/114.1, 18.1; 202/176; 203/DIG. 6, DIG. 9, 158, 87; 196/14.52

[56] References Cited

U.S. PATENT DOCUMENTS

| | | | |
|---|---|---|---|
| 2,752,229 | 6/1956 | Brown et al. | 261/114.1 X |
| 2,826,601 | 3/1958 | Barsky | 203/DIG. 6 X |
| 2,868,524 | 1/1959 | Annable et al. | 261/144.1 X |
| 4,019,964 | 4/1977 | Fickel | 203/DIG. 9 X |
| 4,089,752 | 5/1978 | Hancock, II | 203/DIG. 6 X |
| 4,415,508 | 11/1983 | Aida et al. | 261/114.1 |
| 4,425,285 | 1/1984 | Shimoi et al. | 422/211 X |
| 4,655,798 | 4/1987 | Ruch et al. | 55/64 |
| 5,188,709 | 2/1993 | Kuerston et al. | 196/14.52 |

*Primary Examiner*—Amalia L. Santiago
*Attorney, Agent, or Firm*—Millen, White, Zelano, & Branigan

[57] ABSTRACT

In the absorption of acetylene from a crude gas mixture containing mostly $C_2$ hydrocarbons, a substantially acetylene-free liquid $C_2$ stream is introduced into a mixing chamber located in the column between the feed points for the crude gas mixture and the absorption agent. The $C_2$ stream is distributed into fine droplets as it enters into accumulated absorption agent in the mixing chamber, so that foam is not formed in the absorption column. The mixing chamber can be formed of a mixing tank integrated with a plate.

14 Claims, 4 Drawing Sheets

ABSORPTION COLUMN WITH INTERNAL MIXING CHAMBER FOR ABSORPTION OF ACETYLENE

CROSS-REFERENCE TO RELATED APPLICATION

This is a division of application Ser. No. 07/980,868, now issued as U.S. Pat. No. 5,336,838, filed Nov. 24, 1992, which is a continuation of application Ser. No. 07/933,590, now abandoned, filed Aug. 24, 1992, and is related to a concurrently filed application, "Absorption Columns with External Mixing for Absorption of Acetylene", Ser. No. 07/980,886.

BACKGROUND OF THE INVENTION

This invention relates to a gas absorption process and apparatus, particularly for scrubbing acetylene out of a crude gas mixture containing mostly $C_2$ hydrocarbons.

The invention is especially directed to an improvement in the operation of a plate column, wherein the crude gas mixture is fed into the lower zone of the absorption column; fresh or regenerated absorption agent is fed to the upper zone of the absorption column; loaded absorption agent is drawn off the bottom of the absorption column and is fed to a regeneration stage; a substantially acetylene-free product gas stream is withdrawn from the head of the absorption column, optionally after separation and recycling of a reflux condensate to the absorption column, and wherein a substantially acetylene-free liquid $C_2$ stream is introduced into the absorption column between the respective feed points for the crude gas mixture and the absorption agent.

In the extraction of ethylene from a thermally cracked cut of hydrocarbons, a crude gas mixture is obtained containing mostly $C_2$ hydrocarbons (ethylene, acetylene and optionally ethane). Besides the $C_2$ hydrocarbons, the crude gas mixture may also contain $C_3$ hydrocarbons and/or methane. Acetylene is generally removed from the crude gas mixture by scrubbing with an absorption agent selective for acetylene. In this connection, EP-B 0 158 280, corresponding to U.S. Pat. No. 4,655,798, teaches a process comprising passing an additional feed of a substantially acetylene-free, liquid, $C_2$ stream into the absorption column. Despite the introduction of this acetylene-free $C_2$ stream, foam is formed time and again in the absorption column, and this foam is highly undesirable since it results in downtime and/or the escape of acetylene into the product gas. The formation of both hydrocarbon-rich and hydrocarbon-poor liquid phases, in addition to the vapor phase, are generally responsible for the foam. These two liquid phases are formed when the saturation limit of the absorption agent is exceeded relative to the hydrocarbons present. But foam formation can also occur far below the saturation limit in the absorption column, particularly under unstable operating conditions.

SUMMARY OF THE INVENTION

An object of this invention, therefore, is to provide a process and apparatus in which foam is largely or completely prevented.

Upon further study of the specification and appended claims, further objects and advantages of this invention will become apparent to those skilled in the art.

These objects are achieved according to the invention by introducing fine droplets of the substantially acetylene-free liquid, $C_2$ stream into a pool of absorption agent accumulating in the column. By virtue of the method of introducing the substantially acetylene-free $C_2$ stream into the absorption agent, the $C_2$ stream and this absorption agent are mixed without causing the formation of foam.

This prevention of the foaming of the absorption agent is quite unexpected, and it occurs even if the absorption agent is almost completely saturated with hydrocarbons.

For the process according to the invention, all absorption agents are suitable which exhibit a selective solubilizing power for acetylene as compared to ethylene, such as, for example, N-methylpyrrolidone (NMP) or dimethylformamide (DMF).

The crude gas mixture containing mostly $C_2$ hydrocarbon generally contains on a percent by volume basis about 0.5 to about 4.0 acetylene and about 95.0 to about 99.0 other $C_2$ hydrocarbons.

The substantially acetylene-free liquid $C_2$ stream generally contains in percent by weight basis, less than about 5 ppm, especially less than about 0.5 ppm, acetylene.

The temperature and pressure conditions in the column are generally about 210° to 283°, preferably 238° to 273° K. and about 6.0 to 30.0, preferably 15.0 to 30.0 bar.

The pressure of the substantially acetylene-free liquid $C_2$ stream entering the column must be higher than the pressure of the column at the location of $C_2$ feed point.

Special advantages in the process according to the invention can be produced if the absorption agent is accumulated in a mixing zone which is integrated with a tray (plate) of the absorption column. Into this mixing zone are fed the absorption agent from the plate above and the substantially acetylene-free liquid $C_2$ stream. In this way, the $C_2$ stream is especially well mixed with the absorption agent accumulated in the mixing zone.

As a particular embodiment of the invention, the absorption agent can be introduced from the plate above by an immersion tube in the mixing zone. Also, it is preferred to introduce the substantially acetylene-free liquid $C_2$ stream into the mixing zone at a location below the introduction of the absorption agent, which also increases the efficiency of the mixing step.

In a still further modification of the invention, the substantially acetylene-free $C_2$ stream is preferably introduced at a temperature which is below the temperature of the absorption agent in which said $C_2$ stream is mixed. This serves to cool the absorption agent, thereby increasing the solubilizing power of the absorption agent relative to acetylene. For example, it is preferred that temperature of the $C_2$ stream is about 1° to 20°, preferably 2° to 15° below the temperature of the absorption agent.

The $C_2$ stream is advantageously introduced into the lower two thirds, preferably in the lower half of the absorption column. In a further preferred aspect of the invention, several substantially acetylene-free liquid $C_2$ streams can be fed into the absorption column on several trays. In this way, by introducing several $C_2$ streams with different temperatures, a desired temperature profile can be adjusted in the absorption column.

With additional advantage, the mixing zone can be filled with any type of packing, e.g., structured packing, Raschig rings, etc. In this way, not only is the mixing of the $C_2$ stream and absorption agent improved, but also the gas-liquid contact is more efficient.

In the apparatus aspect of this invention, there is provided an absorption column having several plates, a feed pipe for the crude gas mixture, a feed pipe for fresh and/or regenerated absorbing agent, a feed pipe for the substantially acetylene-free liquid $C_2$ stream, an outlet for the acetylene-free product gas stream, and an outlet for the loaded absorption agent. In addition, the apparatus comprises a mixing tank, open on top, installed in a plate, an immersion tube projecting from an upper plate downwardly into the mixing tank, permitting the absorption agent on an upper plate to fall into the mixing tank, and a feed pipe for the substantially acetylene-free liquid $C_2$ stream installed through the wall of the absorption column and leading into the mixing tank.

The feed pipe for the substantially acetylene-free liquid $C_2$ stream is preferably branched into several outlet pipes in the mixing tank, so as to permit thorough mixing in the mixing tank. In an especially advantageous embodiment, the outlet pipes are furnished with multiple orifices as outlet openings in the nature of a spray head or distributor so that finely divided $C_2$ stream can be passed into the absorbing agent.

As a further modification of the apparatus, multiple feed pipes for accommodating multiple acetylene-free liquid $C_2$ streams are provided at several plate locations in the absorption column. The absorption column in this case contains several plates, each provided with a feed pipe for the substantially acetylene-free liquid $C_2$ stream into a respective mixing tank on each plate.

BRIEF DESCRIPTION OF THE DRAWINGS

Various other objects, features and attendant advantages of the present invention will be more fully appreciated as the same becomes better understood when considered in conjunction with the accompanying drawings, in which like reference characters designate the same or similar parts throughout the several views, and wherein.

DETAILED DESCRIPTION OF THE DRAWINGS

Figure 1:
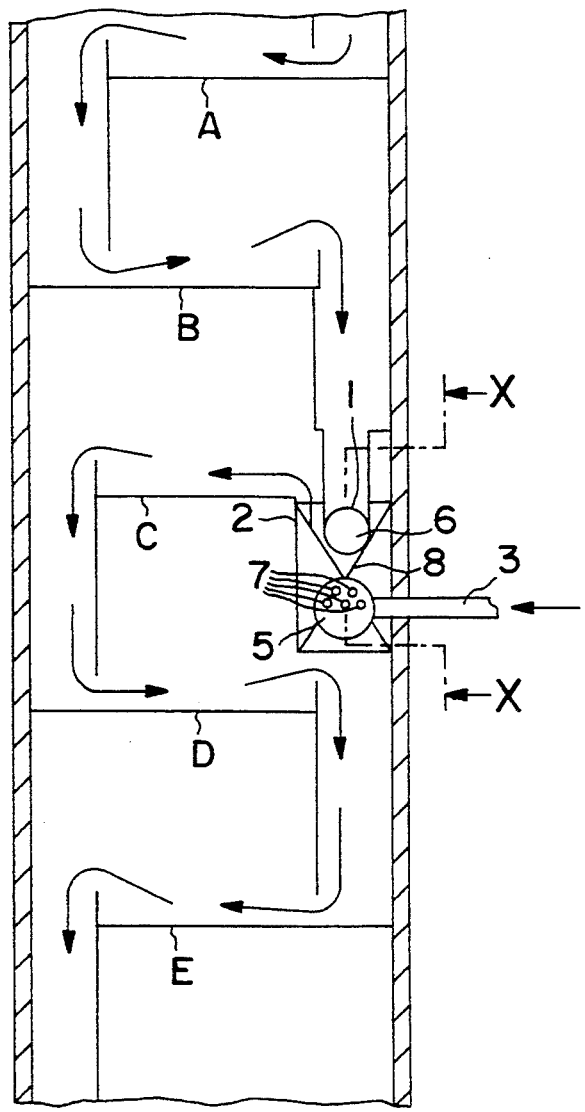
FIG. 1 is a cutaway front vertical schematic of an absorption column according to the invention.

FIG. 1 shows a cutaway of an absorption column wherein plates A, B, C, D and E and G are, for example, bubble plates or sieve plates, each respectively provided with an offset downcomer in the absorption column. The absorption agent falls countercurrent to the rising gas from one plate to the plate lying underneath via a plate downcomer. The direction of the absorption agent flowing downwardly in the absorption column is represented by arrows.

The downcomer of plate B leads into immersion tube 1 which projects into mixing tank 2, provided in plate C. Feed pipe 3 for the substantially acetylene-free liquid $C_2$ stream ends in mixing tank 2 in a cross pipe 4, which is closed with pipe end pieces 5. The absorption agent flows via immersion tube 1 and T-fitting conduit 6 into the mixing tank 2. The substantially acetylene-free liquid $C_2$ stream is introduced into the mixing tank 2 incorporated in a plate 8 via pipe 3, cross pipe 4 and outlet openings 7 in cross pipe 4 and in end piece 5. The substantially acetylene-free liquid $C_2$ stream is evaporated and mixed with the absorption agent accumulated in the mixing zone, i.e., in mixing tank 2. The design of the mixing tank 2 is made taking into consideration the degassing times for the evaporating $C_2$ stream.

Utilizing the $C_2$ stream, colder than the absorption agent, the absorption agent in mixing tank 2 is additionally undercooled. The absorption agent then passes into plate C and according to the arrows, to plate D, E, etc.

Figure 2:
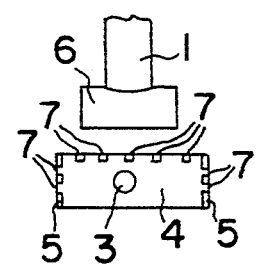
FIG. 2 is a schematic end view of the feed pipe, immersion tube and distributor.

In FIG. 2, immersion tube 1 is illustrated with a cross pipe 6, as well as feed pipe 3 for the $C_2$ stream, cross pipe 4 and end pieces 5.

Figure 3:
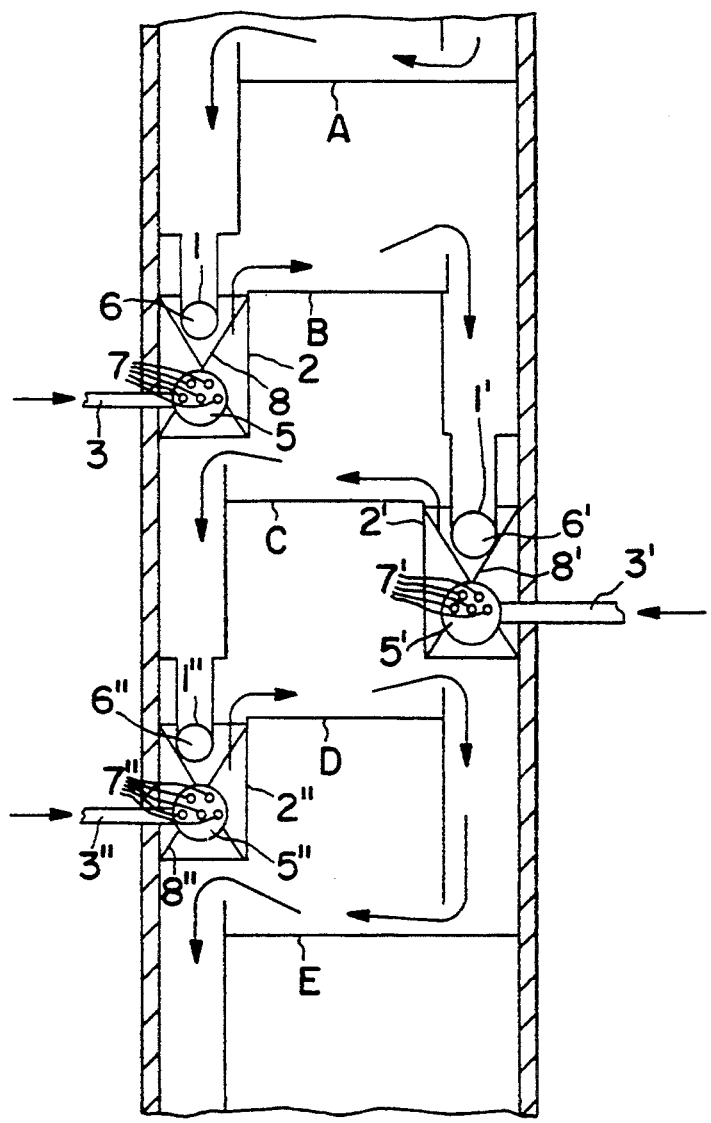
FIG. 3 is a cutaway front vertical schematic of an absorption column according to the invention having multiple feed pipes for multiple acetylene-free liquid $C_2$ streams.

In FIG. 3 the absorption column differs from that of FIG. 1 in that there are multiple feed pipes for the substantially acetylene-free liquid $C_2$ streams, i.e. additional elements 1'-3' and 5'-8' and 1''-3'' and 5''-8''.

Figure 4:
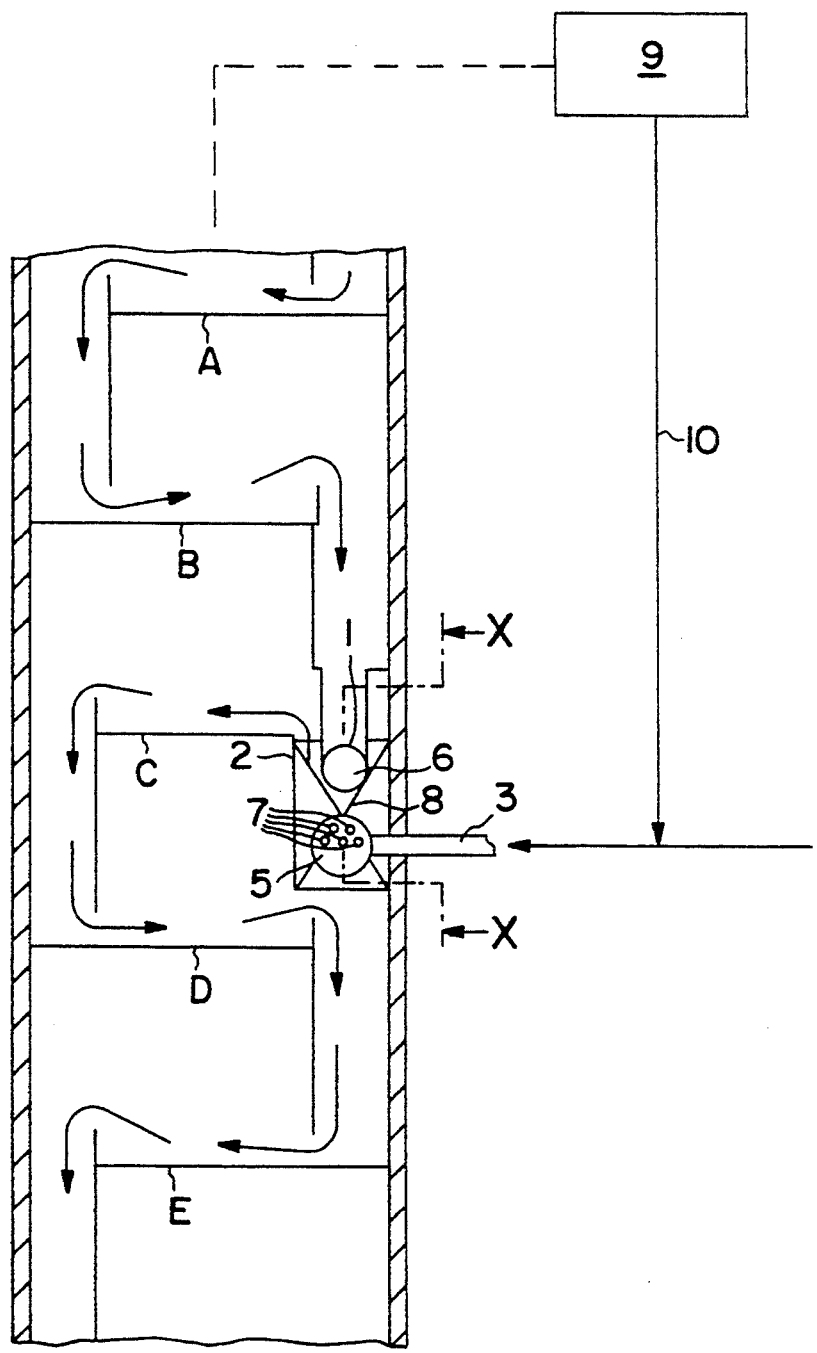
FIG. 4 is a cutaway front vertical schematic of an absorption column according to the invention having a line joining the feed pipe (3) with the condenser (13).

In FIG. 4 the absorption column additionally contains a reflux condenser 9 to which the substantially acetylene-free product gas stream is conducted and a line 10 for withdrawing liquid from the condenser 9 to the feed stream 3.

Figure 5:
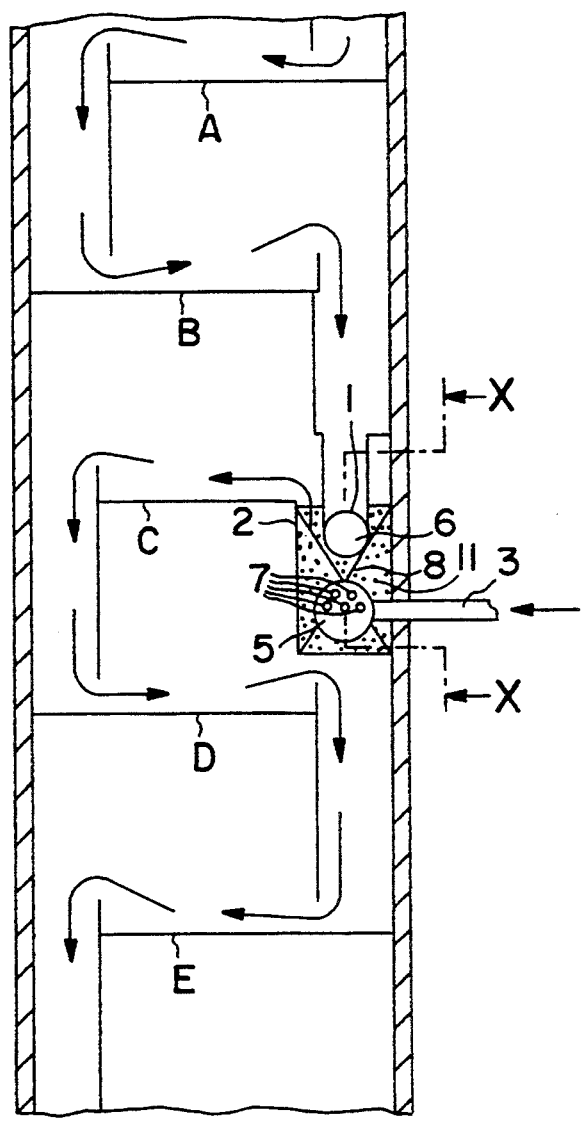
FIG. 5 is a cutaway front vertical schematic of an absorption column according to the invention having a mixing chamber containing packing material.

In FIG. 5 a mixing chamber 8 contains a packing material 11.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

The entire disclosures of all applications, patents and publications, cited above and below, and of corresponding application German P 41 27 988.3, filed Aug. 23, 1991, are hereby incorporated by reference.

EXAMPLES

In tests, dimethylformamide (DMF) was used as the absorption agent.

At a pressure of about 10 bars in the absorption column, a resaturation of the DMF up to about 10 to 40% of complete saturated was obtained as a function of the ethylene/ethane ratio on the respective tray of the absorption column, and at 30 bars, a resaturation of the DMF up to about 15 to 42% was obtained without foam formation occurring at either pressure level and at even at the highest degree of resaturation.

The total number of plates in the absorption column is approximately between 20 and 50, and, for example, an substantially acetylene-free liquid $C_2$ stream can be introduced into an absorption column having 42 plates, at the fifth, tenth, fifteenth and twentieth plate. (The number of plates is counted from the bottom of the absorption column toward the top.)

Specific Example

A crude gas stream with a temperature of 225.0° K. and a pressure of 10.0 bars containing 1.0 vol. % $C_2H_2$
84.0 vol. % $C_2H_4$ 14.0 vol. % $C_2H_6$ and
1.0 vol. % $C_{3+}$
is fed into the absorption column. According to the above described process, a substantially acetylene-free liquid $C_2$ stream is introduced in the absorption column. This substantially acetylene-free $C_2$ stream can be obtained from the $C_2$ reflux stream of product. In this case the substantially acetylene-free $C_2$ stream has the same composition as the overhead $C_2$ product stream:

$C_2H_2$ 1 ppm
$C_2H_4$ 85.7 vol. %
$C_2H_6$ 14.3 vol. %

Alternatively, an external liquid acetylene-free $C_2$ stream can be used as the substantially acetylene-free $C_2$ stream. Such an external substantially acetylene-free $C_2$ stream can be, for example, pure ethylene, e.g., from a $C_2$ cycle of the petrochemical plant, an external substantially acetylene-free $C_2$ stream must be used, if no reflux stream is returned to the top of the absorption column.

This invention is also suitable for the absorption for all acetylene from hydrocarbon streams, for example, for the removal of methyl acetylenes from a $C_3$ stream.

It is also contemplated that this invention will be useful in any gas absorption column, in order to prevent foaming.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In an absorption column suitable for removing acetylene from a crude gas mixture containing mostly $C_2$ hydrocarbons with an absorption agent, said absorption column comprising a plurality of plates with means for the flow of liquid from each plate to the plate below it, a feed pipe suitable for the crude gas mixture, a feed pipe suitable for regenerated absorbing agent, the improvement wherein the column further comprises at least one feed pipe suitable for a substantially acetylene-free liquid $C_2$ stream, an outlet suitable for an acetylene-free product gas stream, and an outlet suitable for loaded absorption agent, at least one mixing chamber (2), open on top, incorporated in at least one plate of said plurality, positioned below the absorbing agent feed pipe and above the crude gas mixture feed pipe, and at least one immersion tube (1) projecting downwardly from the plate above said mixing chamber into said mixing chamber permitting absorption agent from a plate immediately above said at least one plate incorporating the mixing chamber to fall into said mixing chamber (2), wherein the at least one feed pipe (3) suitable for the substantially acetylene-free liquid $C_2$ stream entering the absorption column leads into said mixing chamber (2) and the end of the at least one feed pipe (3) leading into said mixing chamber has multiple liquid outlets to the mixing chamber.

2. An absorption column according to claim 1, said absorption column comprising two or more feed pipes (3) suitable for the substantially acetylene-free liquid $C_2$ streams and two or more mixing chambers (2), each of said two or more feed pipes (3) leading into a different mixing chamber on a different plate in the column.

3. An adsorption column according to claim 1, wherein said at least one mixing chamber is filled with packing.

4. An adsorption column according to claim 2, wherein said two or more mixing chambers are filled with packing.

5. The absorption column of claim 2, wherein the end of each of the two or more feed pipes (3) leading into different mixing chambers is terminated with multiple liquid outlets to the respective mixing chamber.

6. The absorption column of claim 1, wherein the column further comprises a reflux condenser and a recycle line connecting the liquid outlet of the reflux condenser with at least one of the at least one feed pipe(s) (3) suitable for the substantially acetylene-free liquid $C_2$ stream.

7. The absorption column of claim 1, wherein the at least one feed pipe (3) ends in at least one mixing chamber below the outlet of the at least one immersion tube.

8. In an absorption column suitable for removing acetylene from a crude gas mixture containing mostly $C_2$ hydrocarbons with an absorption agent, said absorption column comprising: a plurality of plates with means for the flow of liquid from each plate to the plate below it, a feed pipe suitable for the crude gas mixture, a feed pipe suitable for regenerated absorbing agent, the improvement wherein the absorption column further comprises at least one feed pipe suitable for a substantially acetylene-free liquid $C_2$ stream, an outlet at the head of the column suitable for an acetylene-free product gas stream, and an outlet suitable for loaded absorption agent, at least one mixing chamber (2), open on top, incorporated in at least one plate of said plurality, which is positioned below the absorbing agent feed pipe and above the crude gas mixture feed pipe, at least one immersion tube (1) projecting downwardly from the plate above said at least one mixing chamber into said mixing chamber permitting absorption agent from a plate immediately above said at least one plate incorporating at least one mixing chamber to fall into said at least one mixing chamber (2), wherein the at least one feed pipe (3) suitable for the substantially acetylene-free liquid $C_2$ stream entering the absorption column leads into said at least one mixing chamber (2), and a reflux condenser having a recycle line connecting the liquid outlet of the reflux condenser with at least one of the at least one feed pipe(s) (3) suitable for the substantially acetylene-free liquid $C_2$ stream.

9. An absorption column according to claim 8, said absorption column comprising two or more feed pipes (3) suitable for two or more substantially acetylene-free liquid $C_2$ streams and two or more mixing chambers (2), each of said two or more feed pipes (3) leading into a different mixing chamber on a different plate in the column.

10. An absorption column according to claim 8, wherein said at least one mixing chamber is filled with packing.

11. An absorption column according to claim 9, wherein said two or more mixing chambers are filled with packing.

12. The absorption column of claim 8, wherein the end of at least one feed pipe (3) leading into said at least one mixing chamber has multiple liquid outlets to the mixing chamber.

13. The absorption column of claim 9, wherein each of the two or more feed pipes (3) leading into a different mixing chamber has at its end multiple liquid outlets to the respective mixing chamber.

14. The absorption column of claim 8, wherein the at least one feed pipe (3) discharges into said at least one mixing zone below the outlet of the at least one immersion tube.

* * * * *